(12) United States Patent  
Buzzard et al.

(10) Patent No.: US 6,939,352 B2  
(45) Date of Patent: Sep. 6, 2005

(54) HANDLE DEPLOYMENT MECHANISM FOR MEDICAL DEVICE AND METHOD

(75) Inventors: Jon Buzzard, Miramar, FL (US); Frederick Feller, III, Margate, FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/975,873

(22) Filed: Oct. 12, 2001

(65) Prior Publication Data

US 2003/0167060 A1 Sep. 4, 2003

(51) Int. Cl.$^7$ .............................................. A61F 11/00
(52) U.S. Cl. ....................................... 606/108; 623/1.11
(58) Field of Search ............................... 606/108, 191, 606/192, 194, 195, 198, 205, 207; 623/1.1

(56) References Cited

U.S. PATENT DOCUMENTS

| | | | |
|---|---|---|---|
| 4,665,918 A | | 5/1987 | Garza et al. |
| 4,990,151 A | | 2/1991 | Wallsten |
| 5,026,377 A | | 6/1991 | Burton et al. |
| 5,290,310 A | * | 3/1994 | Makower et al. ........... 606/213 |
| 5,312,351 A | * | 5/1994 | Gerrone ..................... 604/117 |
| 5,391,172 A | | 2/1995 | Williams et al. |
| 5,433,723 A | * | 7/1995 | Lindenberg et al. ........ 606/198 |
| 5,601,568 A | * | 2/1997 | Chevillon et al. .......... 606/108 |
| 5,704,914 A | * | 1/1998 | Stocking et al. ........ 604/164.07 |
| 5,707,376 A | | 1/1998 | Kavteladze et al. |
| 5,749,921 A | * | 5/1998 | Lenker et al. ............. 623/1.42 |
| 5,759,186 A | * | 6/1998 | Bachmann et al. ......... 606/108 |
| 5,776,142 A | * | 7/1998 | Gunderson ................. 623/1.11 |
| 5,782,855 A | | 7/1998 | Lau et al. |
| 5,868,755 A | | 2/1999 | Kanner et al. |
| 5,891,154 A | | 4/1999 | Loeffler |
| 5,906,619 A | * | 5/1999 | Olson et al. ................ 606/108 |
| 5,944,727 A | | 8/1999 | Ahari et al. |
| 5,968,052 A | | 10/1999 | Sullivan, III et al. |
| 6,019,778 A | | 2/2000 | Wilson et al. |
| 6,143,021 A | | 11/2000 | Staehle |
| 6,146,415 A | | 11/2000 | Fitz |
| 6,190,360 B1 | | 2/2001 | Iancea et al. |
| 6,203,550 B1 | * | 3/2001 | Olson ......................... 606/108 |
| 6,517,569 B2 | | 2/2003 | Mikus et al. |
| 6,613,014 B1 | | 9/2003 | Chi |
| 2001/0051822 A1 | | 12/2001 | Stack et al. |
| 2002/0004663 A1 | | 1/2002 | Gittings et al. |

FOREIGN PATENT DOCUMENTS

| | | |
|---|---|---|
| EP | 0 873 733 A1 | 11/1998 |
| EP | 0 876 804 A1 | 11/1998 |
| FR | 2 797 781 A1 | 3/2001 |
| WO | WO 98/11646 A1 | 3/1998 |
| WO | WO 00/18330 | 4/2000 |
| WO | WO 02/087470 A1 | 7/2002 |
| WO | WO 02/087470 A1 | 11/2002 |

OTHER PUBLICATIONS

European Search Report EP 02 25 7071 dated Dec. 8, 2003 with Annex to the European Search Report.

* cited by examiner

Primary Examiner—Julian W. Woo  
Assistant Examiner—Victor X Nguyen  
(74) Attorney, Agent, or Firm—Michael W. Montgomery

(57) ABSTRACT

A system for delivering at least one medical device to a desired location for treatment, and then selectively deploy it in position, includes an improved handle. One of the possible features of the handle may be to selectively hold the delivery system components at any desired configuration during deployment and positioning of the medical device. Another possible feature of the handle may be more than one mode of operation, in which the deployment of the medical device can selectively proceed at more than one speed.

11 Claims, 10 Drawing Sheets

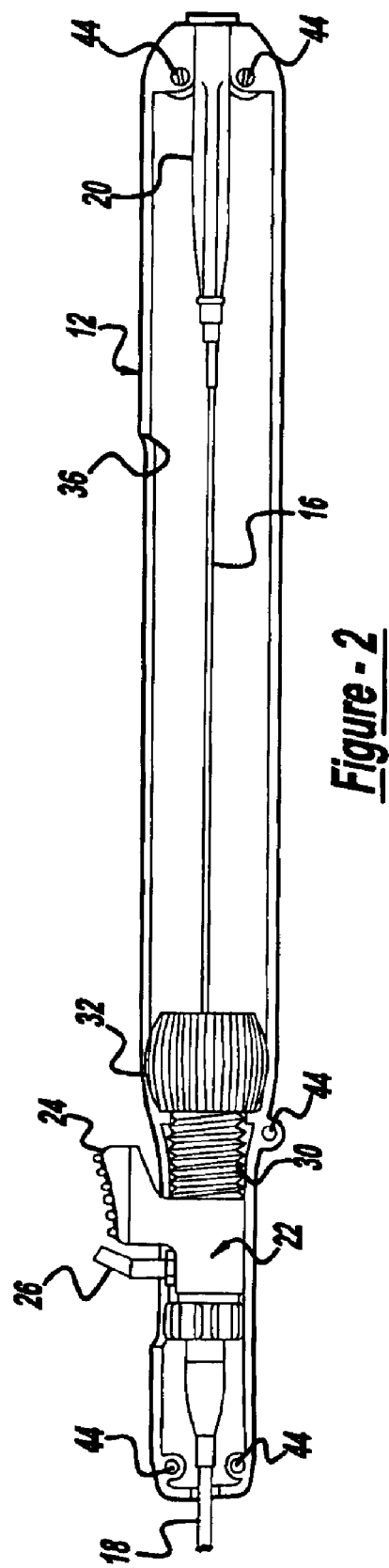
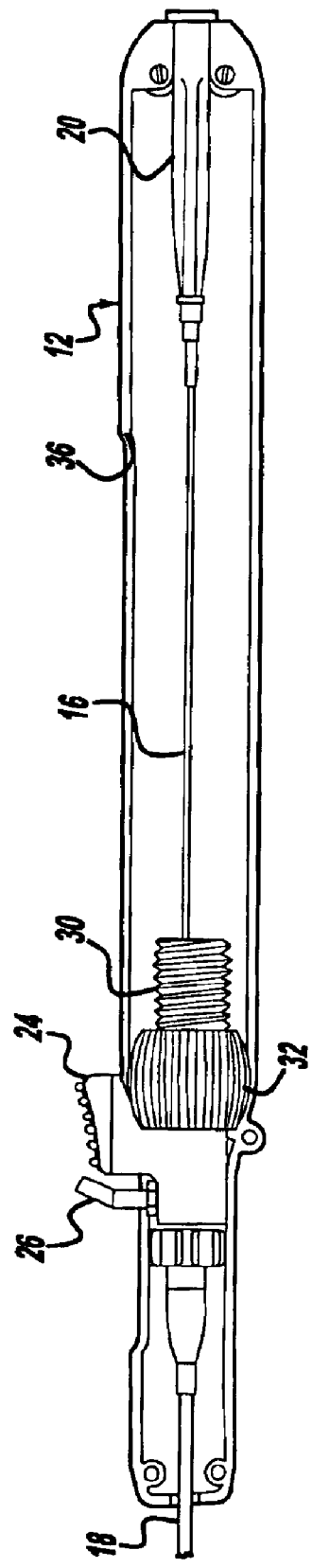

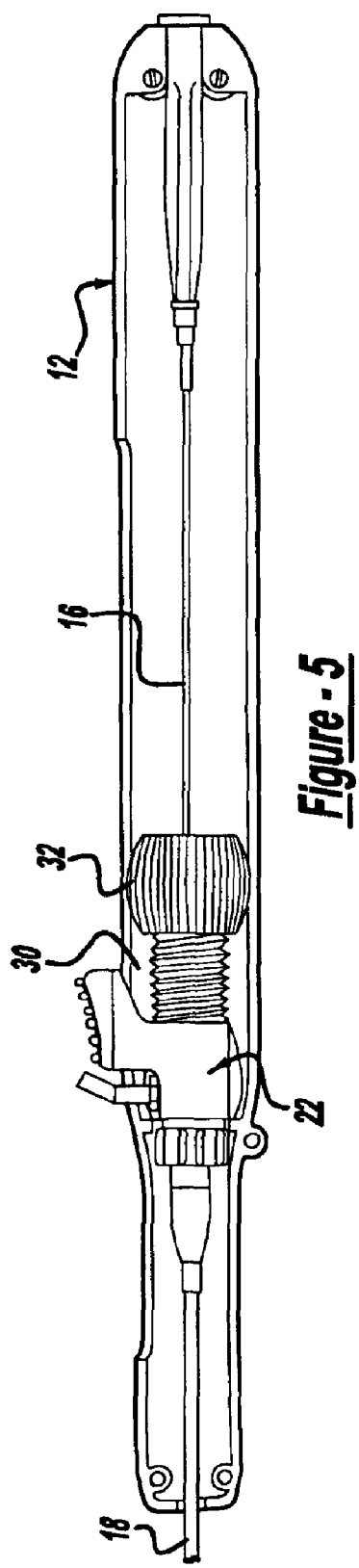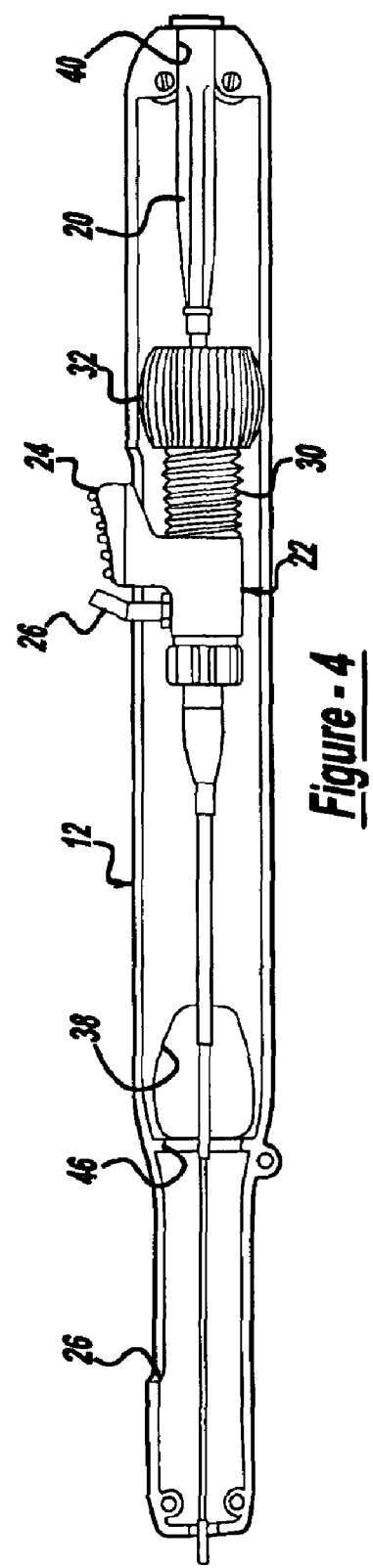

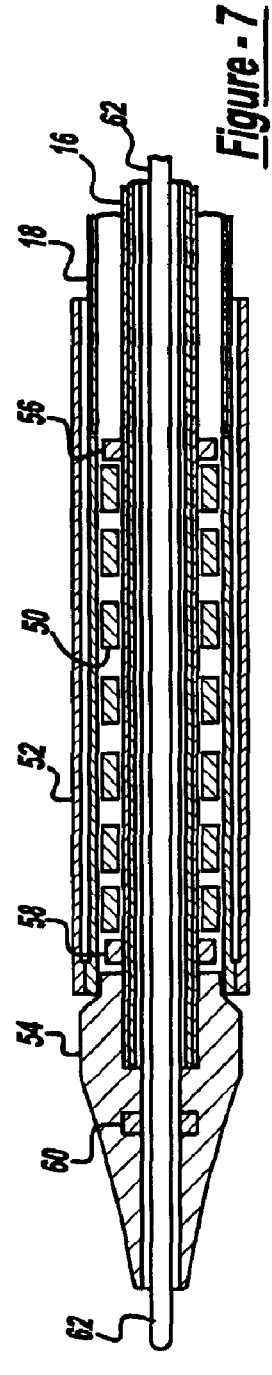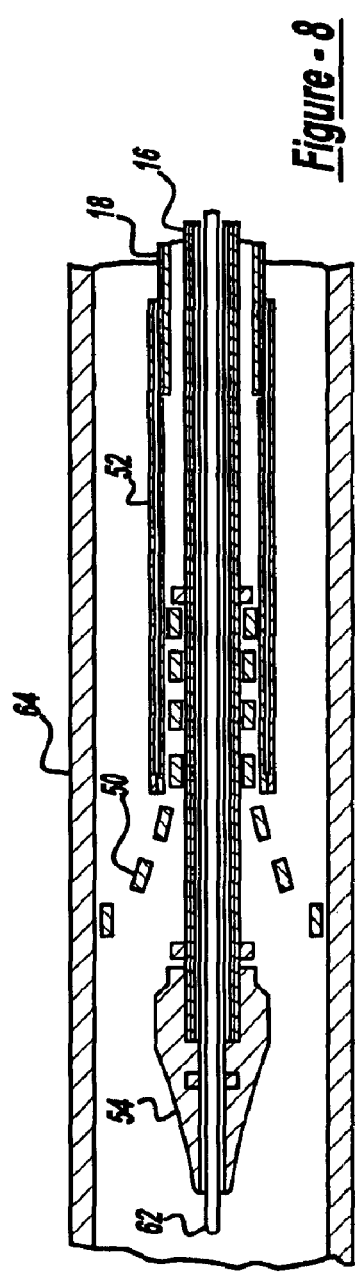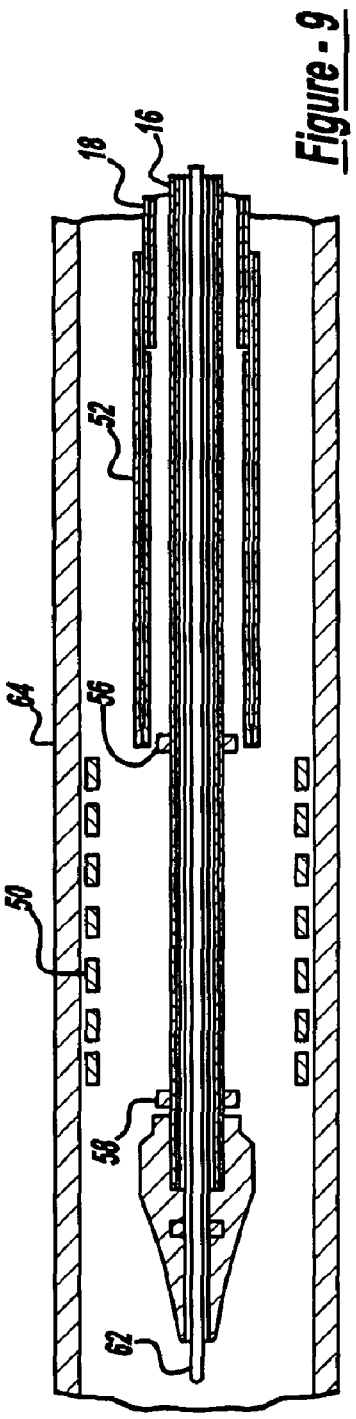

HANDLE DEPLOYMENT MECHANISM FOR MEDICAL DEVICE AND METHOD

BACKGROUND AND SUMMARY OF THE INVENTION

1. Technical Background

The present invention relates generally to medical devices, and more particularly to a medical device delivery system with an improved two-way handle having a compound mechanism.

2. Discussion

The present invention involves medical devices, and also the delivery systems used to convey them to a desired location for treatment, and then deploy them in position. Many such medical devices are resiliently compressed to a smaller initial size for containment, protection, storage and eventual delivery from inside a catheter system. Upon deployment, the medical devices may resiliently expand to a larger deployed size.

A successful example of a delivery catheter system, in this case for a self-expanding stent, is described in U.S. Pat. No. 6,019,778 entitled "Delivery Apparatus For A Self-Expanding Stent," to Wilson et al. issued Feb. 1, 2000. The disclosure of this patent is incorporated by reference in the present application, and generally discloses a flexible catheter system shown in a representative diagrammatic form in FIG. 10, including coaxially arranged inner and outer catheter members, each having a hub affixed to its proximal end. The outer sheath is described in the '778 patent as an elongated tubular member having distal and proximal ends, which is made from an outer polymeric layer, an inner polymeric layer, and a braided reinforcing layer between them. The inner shaft is described in the '778 patent as being located coaxially within the outer sheath and has a flexible tapering distal end, which generally extends distally beyond the distal end of the outer sheath. The inner shaft member also is shown as including a stop which is positioned proximal from the distal end of the outer sheath. A self-expanding stent is located within the outer sheath, and is located between the stop on the inner shaft member and the outer sheath distal end. To deploy the stent the outer sheath is withdrawn by a physician in a proximal direction, while the inner shaft member is held in position.

Additional examples of different types of known self-expanding stent delivery systems are shown in U.S. Pat. No. 4,580,568 issued to Gianturco on Apr. 8, 1986; as well as U.S. Pat. No. 4,732,152 issued to Wallsten et al. Mar. 22, 1988.

In operation, these known medical device delivery systems are generally advanced within a body of a patient along a desired vascular path or other body passageway, until the medical device within the catheter system is located at a desired site for treatment. While watching the relative positions of the medical device and the catheter system components with respect to a stenosis on a video x-ray fluoroscopy screen, the physician holds the proximal hub attached to the inner shaft member in a fixed position with one hand, while simultaneously gently withdrawing the proximal hub attached to the outer tubular sheath with the other hand.

For several reasons, this deployment operation may require some measure of delicate skill. For example, among these reasons is the dynamic blood flow at the desired site for treatment, which may be further disrupted by the presence of a lesion or stenosis to be treated. Another factor is the gradual resilient expansion of a medical device as the outer sheath is retracted. This gradual expansion presents an opportunity for a possible reverse "watermelon-seed" phenomenon to occur. This reverse watermelon-seed effect may cause the resilient medical device to tend to push the outer sheath back in a proximal direction with a force that tends to follow a curve similar shown in FIG. 15.

As a result, the physician may need to accurately hold the two proximal hubs in a specific relative position, holding them against this expansion force, while attempting to very accurately position the medical device up until contact with the anatomy. One of the possibilities that may affect the positioning of the deployed medical device is that the inner shaft should preferably be held stationary in the desired position. If the physician's hand that holds the inner shaft hub does inadvertently move during deployment, it is possible that the medical device may be deployed in a non-optimum position.

Another possible factor is that the inner and outer catheter shaft members, like any other elongated object, do not have infinite column strength, which may present an opportunity for the position and movement of each proximal hub to differ from the position and movement of the respective distal ends of the inner and outer shaft members. Yet another factor is that the position of the medical device may be adjusted up until the point at which a portion of the expanding portion of the medical device touches the sidewalls of the body passage, so that the position of the medical device should preferably be carefully adjusted until immediately before a portion of the medical device touches the anatomy.

Some known catheter systems require two-handed operation, such as those with a pair of independent hubs, one hub on the inner and outer shaft member, respectively. Other known catheter systems include a pistol and trigger grip, with a single mode of deployment, involving a single trigger pull to deploy the associated medical device.

Accordingly, although physicians may be capable of operating such known systems with great skill, it is desirable to provide an improved catheter delivery system capable of facilitating easier and more accurate deployment and positioning of resiliently expansive medical device.

In addition, it is desirable to provide an advanced catheter deployment mechanism having two modes of operation. In the first mode of operation, the delivery mechanism preferably provides a precisely adjustable link between the inner and outer catheter shaft members, such that the relative position of the outer sheath with respect to the inner catheter shaft member can be precisely and selectively adjusted. Yet at any selected position, the delivery mechanism should preferably maintain this selected relative position of the inner and outer catheter shaft members, while resisting any force that may be present tending to move the inner or the outer catheter shaft members with respect to the other. In a second mode of operation, the delivery mechanism should preferably enable the physician to rapidly withdraw the outer tubular sheath with respect to the inner catheter shaft member preferably in a proximal direction with a single easy motion.

The present invention provides such a desirable medical device delivery mechanism, with an integrated handle replacing the functions of the separate proximal hubs of the prior inner and outer catheter shaft members, and also providing desired dual modes of operation.

These and other various objects, and advantages and features of the invention will become apparent from the following description and claims, when considered in conjunction with the appended drawings.

BRIEF DESCRIPTION OF THE DRAWINGS

FIG. 2 is a partial longitudinal cross-sectional view of a medical device delivery system arranged according to the present invention in an initial configuration;

FIGS. 3–5 are partial longitudinal cross-sectional views of the medical device delivery system of FIG. 2, in various operating configurations;

FIGS. 7–9 are partial cross-sectional views of a distal end portion of the medical device delivery system of FIG. 2, corresponding to various operating configurations;

DETAILED DESCRIPTION OF THE PREFERRED EMBODIMENTS

Figure 1:
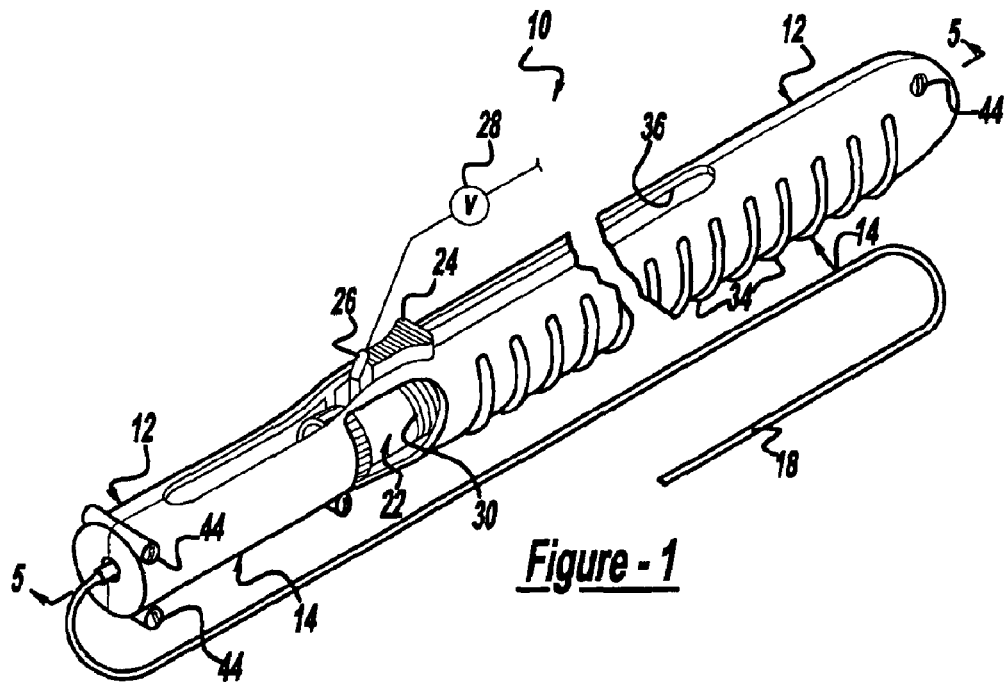
FIG. 1 is an external perspective view of a medical device delivery mechanism and handle, arranged according to the principles of the present invention.

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, a medical device delivery system is depicted, with one of the preferred embodiments of the present invention being shown at 10. The illustrated stent delivery catheter system 10 of course depicts only one of many different medical device delivery systems designs that are within the scope of the present invention. For clarity and convenience, the present detailed description will only describe such an example of a delivery system for stents.

One possible medical device delivery system that may be used with the present invention is any appropriate system in which an outer sheath is provided, surrounding an inner shaft. A medical device may be carried within the outer sheath during delivery to a desired site for treatment, where the outer sheath may be retracted, while the inner shaft and medical device are held in place.

The novel concept of the present invention may also be used for medical device delivery systems in which the motion of the operator to deploy the medical device is selected from any suitable possibility, including axial motion in the proximal direction or the distal direction, or a rotational motion, a trigger actuator, a gear mechanism, or any other type of actuator that may be preferred, depending upon a particular application. Indeed, the present unique concept may be used for medical device delivery systems in which the medical device is deployed in any suitable manner, including retracting an outer sheath in a proximal direction or a distal direction, or uncovering a medical device in various ways, including withdrawing portions of outer sheath members in proximal and distal directions, simultaneously or sequentially.

The present invention may provide several advantages individually, or any combination of such advantages, including for example: (i) single-handed operation of the medical device delivery system; (ii) a mechanism providing leverage or mechanical advantage, to adjust or reduce the forces needed to operate the system; (iii) improved accuracy in positioning the medical device during deployment; (iv) a capability of holding the delivery system components in a fixed relative position during an intermediate point in deploying a medical device; and (v) multiple operational modes of operation, including for example a first mode of fine and precise control of the deployment process, and a second mode of rapid and easy deployment.

Figure 6:
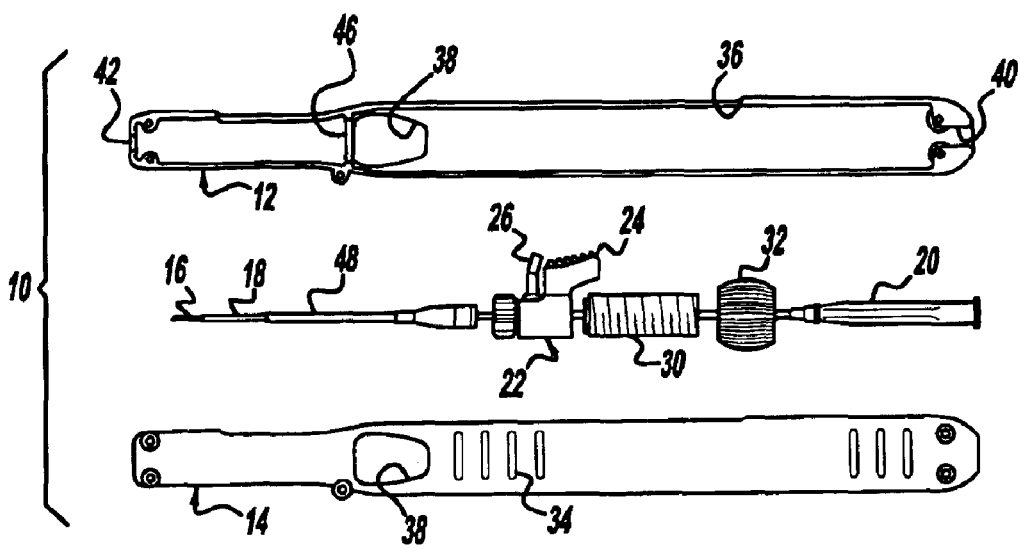
FIG. 6 is an exploded view of the medical device delivery system components.
Figure 10:
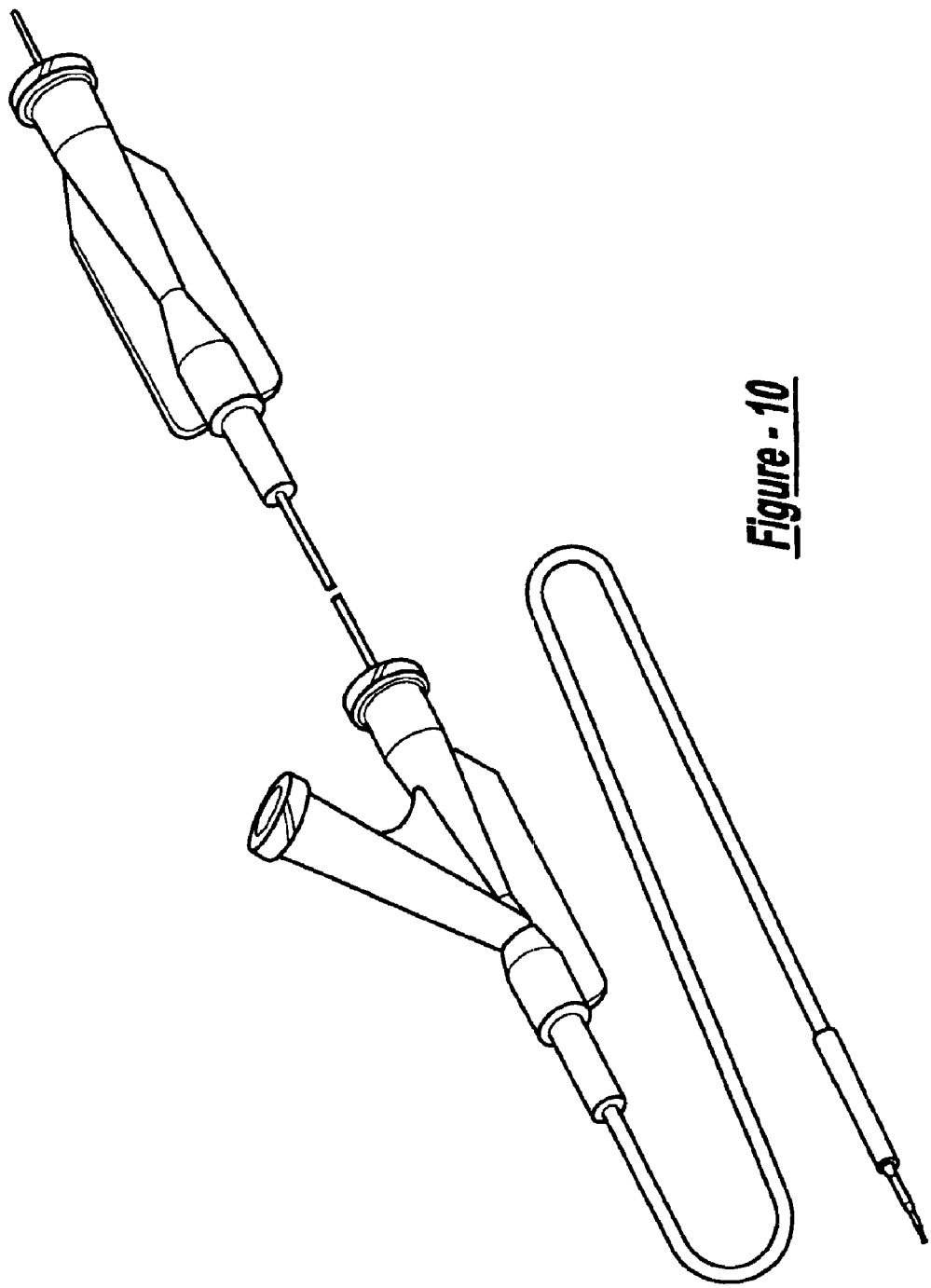
FIG. 10 is an external perspective view of a known medical device delivery system.
Figure 11:
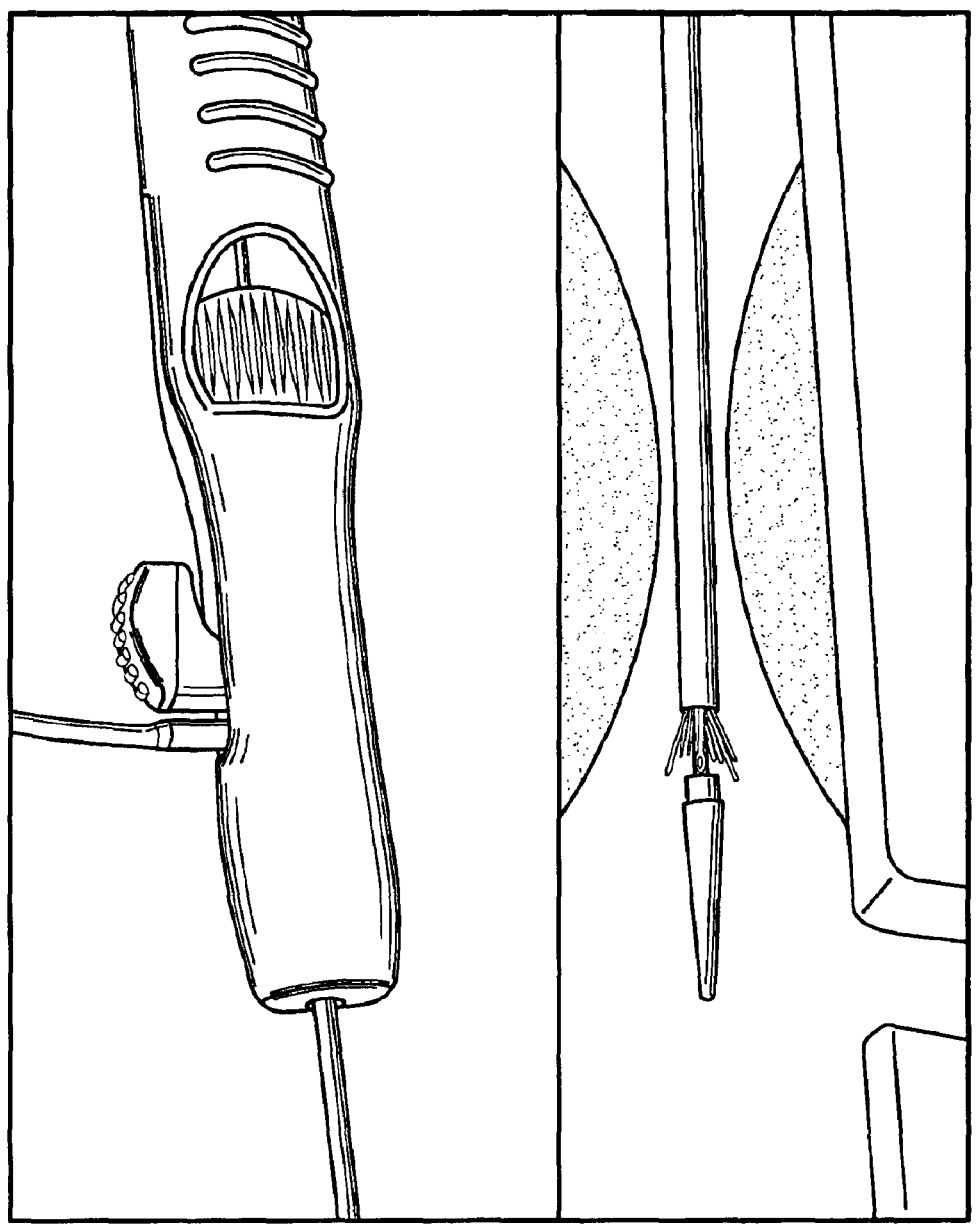
FIGS. 11–14 are perspective views of proximal and distal ends of a medical device delivery system arranged according to the principles of the present invention, in various operating configurations.
Figure 12:
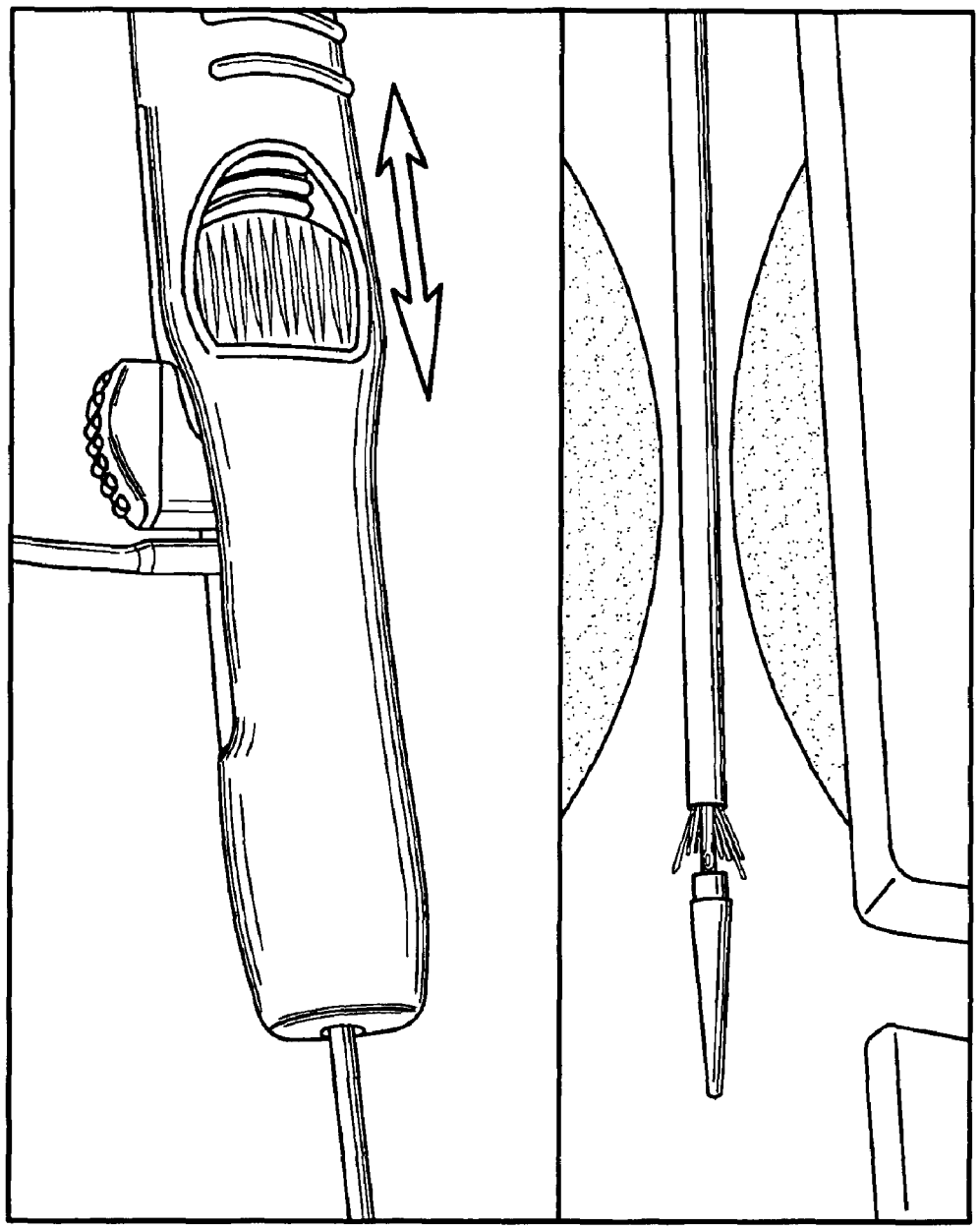
Figure 13:
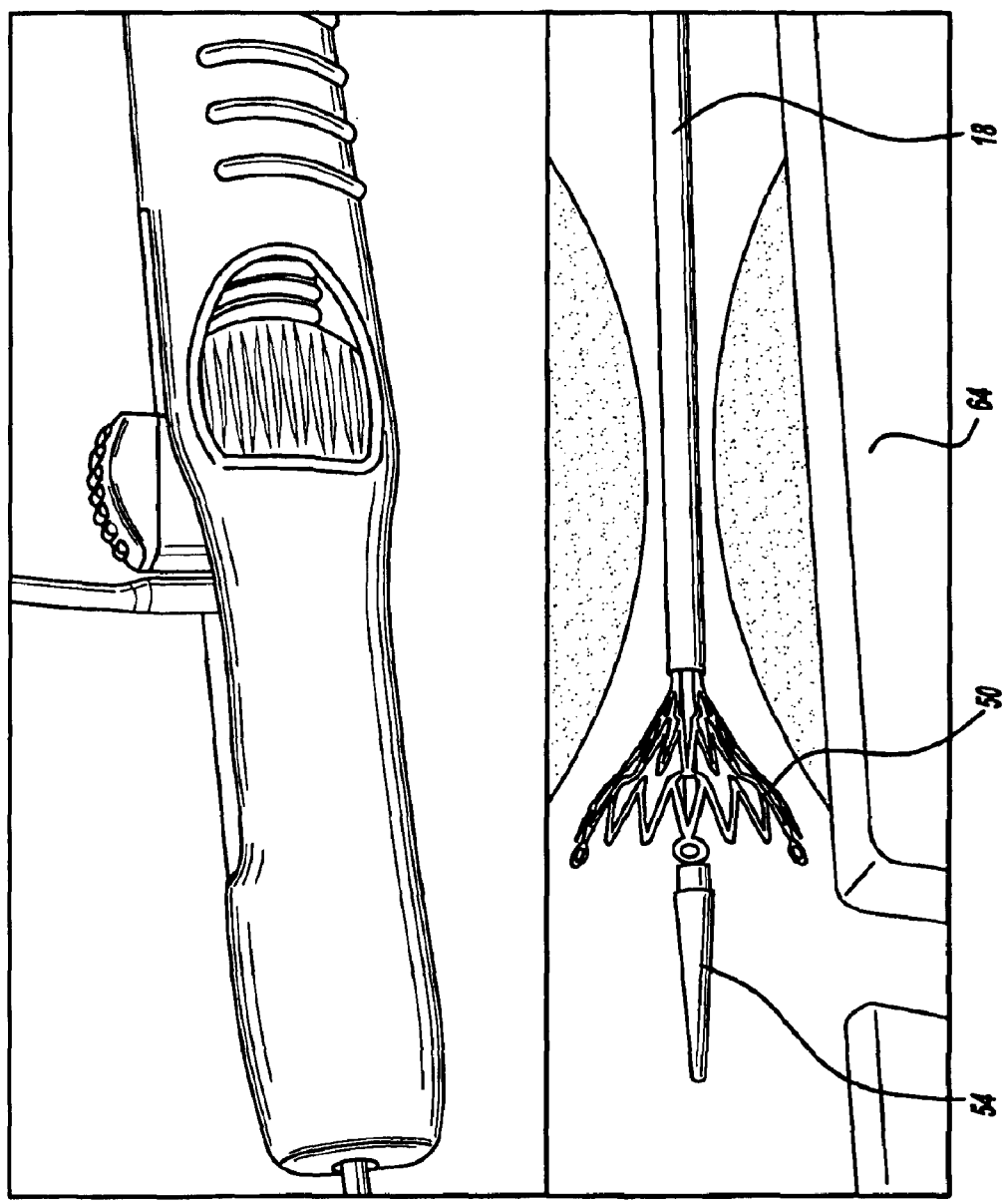
Figure 14:
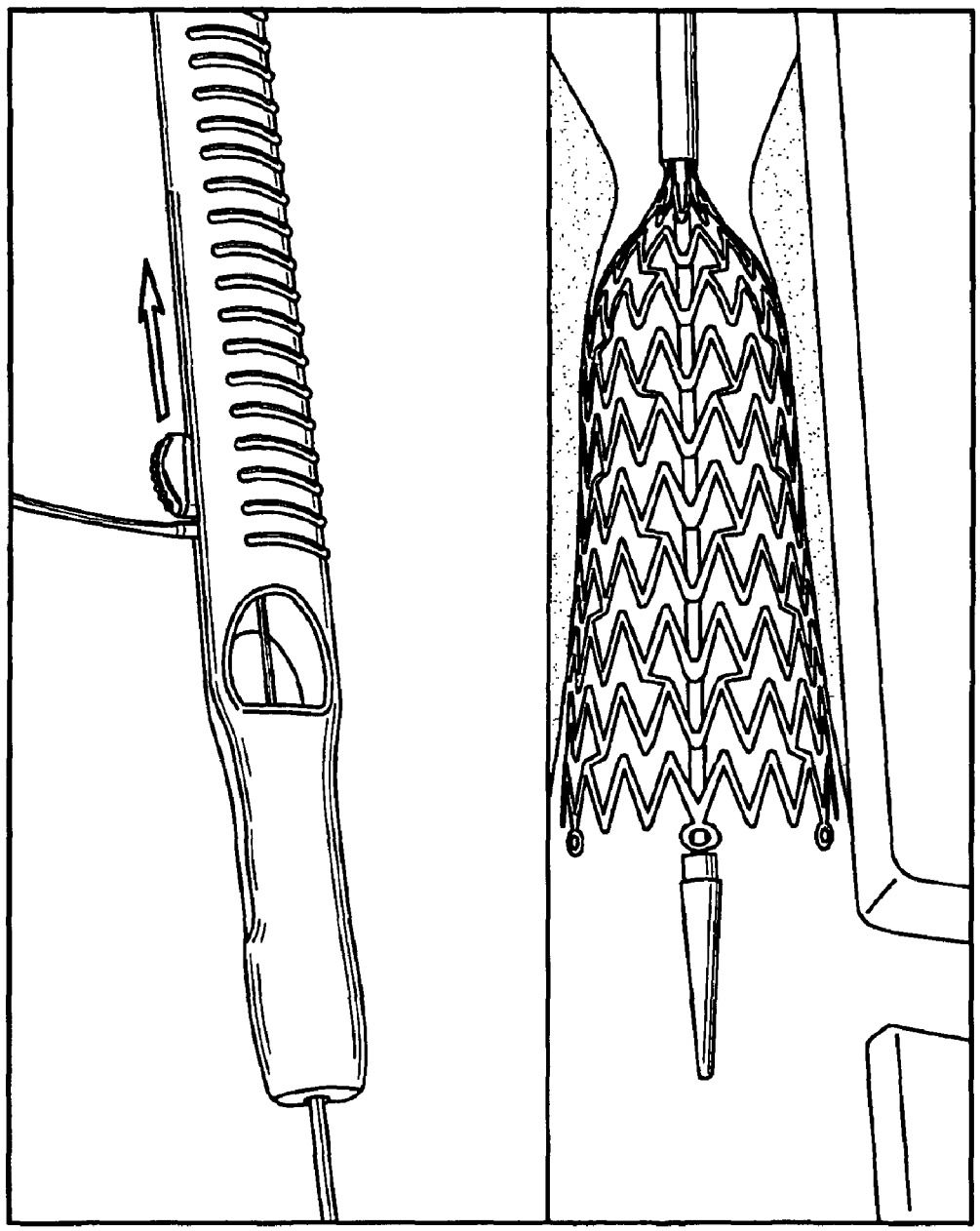
Figure 15:
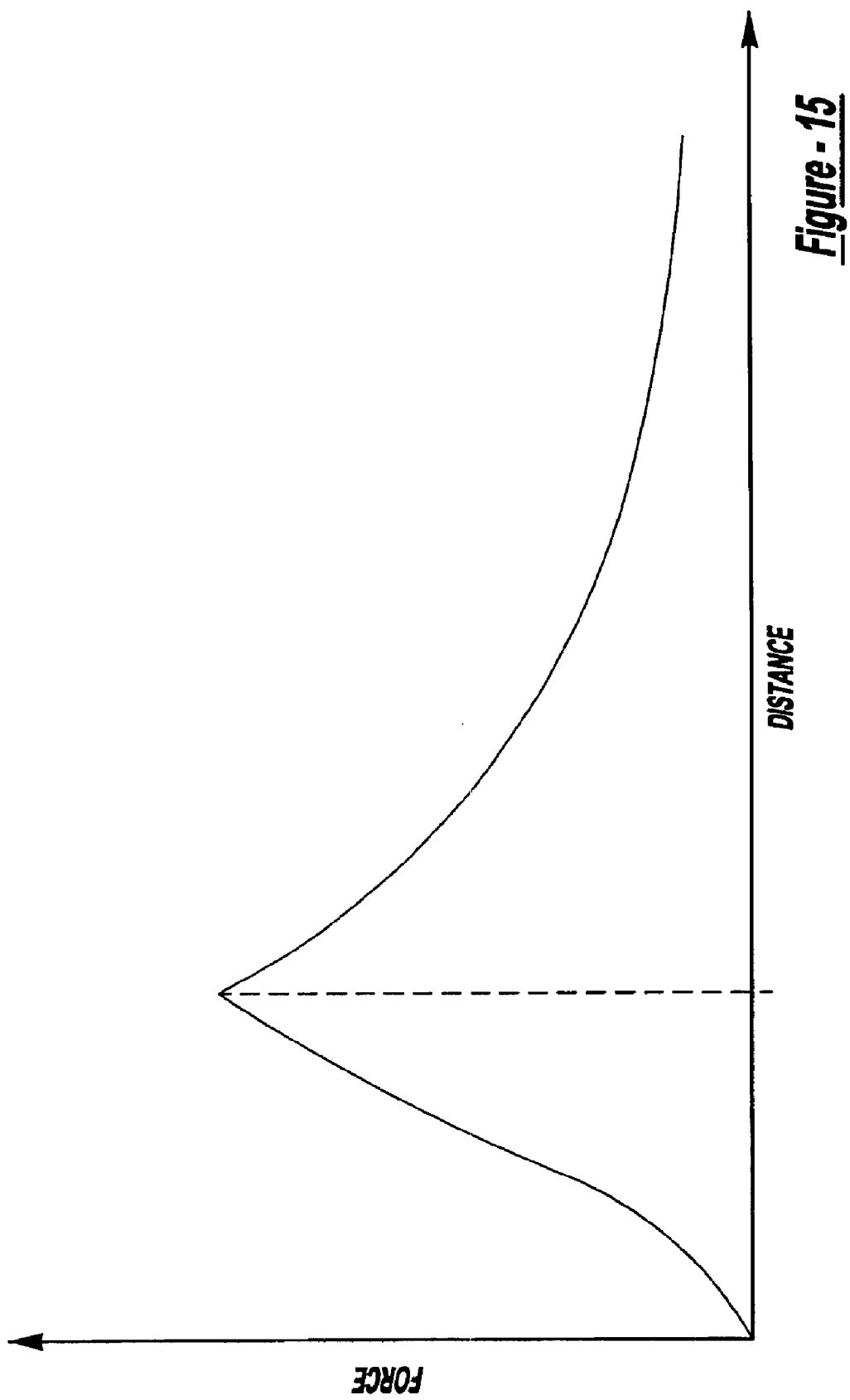
FIG. 15 is a diagrammatic example of a possible graph showing total resistive forces with respect to positional distance, of a medical device delivery system arranged according to the principles of the present invention.

The particular embodiment 10 of the present invention selected for illustration in the drawings includes a handle, shown in detail in FIGS. 1-6. A first and second main body housing 12 and 14 are arranged in a side-by-side configuration, as shown for example in FIG. 1. Other components include inner and outer shaft members 16 and 18 respectively, an anchoring member 20, a proximal hub 22 with an actuator or knob 24 and a corresponding flush lumen tube 26 and valve 28, as well as a threaded base member 30 and a rotating finger ring 32.

The main body housings 12 and 14 each preferably have several gripping knurls 34 for providing a physician with a good gripping surface, a longitudinal slot 36 defining a channel for sliding the movable actuator 24 and limiting the extent of possible travel for the actuator 24 and proximal hub assembly 22, a side opening 38 through which a physician can operate the rotating finger ring 32, a proximal anchoring aperture 40 adapted to capture a portion of the anchoring member 20, a distal shaft aperture 42 through which the inner and outer shaft members 16 and 18 extend, and several openings for receiving fasteners 44 to hold the main body housings 12 and 14 together. The main body housings 12 and 14 also define a circular annular bearing shelf or shoulder 46. A distal surface of rotating finger ring 32 touches this shoulder 46 in an initial configuration, and rotation of the rotating finger ring 32 causes it to advance along threaded base 30 and press on shoulder 46, resulting in very precise and sensitive withdrawing movement of outer shaft member 18 in a proximal direction.

In the particular assembly shown in the drawings, main body housings 12 and 14 are held together by fasteners 44. Anchor aperture 40 fixedly receives anchor 20, which is affixed to the proximal end of inner shaft member 16. A proximal end of outer shaft member 18 is affixed to proximal hub 22, with a flexible strain relief 48 protecting the joint. In the preferred initial configuration, proximal hub 22 is affixed to threaded base 30, which rotatably carries rotating finger ring 32, which bears on the shoulder 46 of main body housing 12.

The preferred dual operation of the present invention is accomplished by enabling movement of outer shaft member 18 with respect to inner shaft member 16 in two ways. First, by rotating the finger ring 32 to cause it to advance on threaded base 30 and press against shoulder 46, such that the entire assembly of threaded base 30, proximal hub 22 and outer shaft member 18 withdraw proximally with respect to main body housing 12 and 14, and thus with respect to inner shaft member 16. Second, by simply grasping knob 24 and pulling or pushing it within slot 36. The first method allows precise and sensitive adjustment, while the second method allows relatively large-scale and rapid movement.

At the distal end of the medical device delivery system, shown in detail in FIGS. 7–9, distal ends of the inner and outer shaft members 16 and 18 are depicted, as well as whatever medical device is selected, in this particular case a stent 50. The stent 50 shown in the drawings is of the self-expanding type, and may be captured within a tubular capsule 52 affixed to outer shaft member 18. The distal end of inner shaft member 16 may be provided with a flexible tapering distal tip 54. At least a proximal annular stop 56, and preferably also a distal annular ring 58, are affixed to inner shaft member 16. The stop 56 and ring 58, as well as a distal marker 60 that may be provided, are preferably radiopaque.

In addition, the inner shaft member 16 assembly, including anchor 20, inner shaft member 16 and distal tip 54, may preferably be provided with a through lumen adapted to receive a guidewire 62.

In operation, the medical device delivery system 10 is advanced via a body passageway, preferably along a guidewire 62, until the stent 50 is located within a desired site for treatment. A physician gently rotates the finger ring 32 to slightly pull back outer shaft member 18. At this point, a small portion of the stent 50 may expand slightly. The handle of the present invention comfortably holds the delivery system 10 in this intermediate configuration, allowing the physician time and flexibility of procedure to selectively optimize the position of the stent 50 within the desired site. This precise adjustment of the position of the stent 50, before any portion of the stent 50 touches the body passage or vessel 64 in a manner that might inhibit further positional adjustment, is preferable.

When the physician is satisfied with the positioning, the finger ring 32 may be further rotated to cause a distal end of the stent 50 to gently contact the vessel 64. When such contact occurs, and the stent is expanded sufficiently to independently hold its position, it is desirable to rapidly and completely withdraw the outer shaft member 18. To do so, the physician grasps the knob 24 and pulls it back along slot 36. The outer shaft member 18 may thus be withdrawn as quickly as the physician wishes.

Various materials may be selected for the components of the present invention, including any material having the desirable performance characteristics. In the particular embodiment shown in the drawings, the inner and outer shaft members 16 and 18, strain relief 48, and distal tip 54 may be made of any biocompatible and suitably flexible yet sufficiently strong material, including polymers of various types. Possible selections for such materials include nylons or polyamides, polyimides, polyethylenes, polyurethanes, polyethers, polyesters, etc. In the alternative, some portion or all of the inner and/or outer shaft member 16, 18 may be formed of a flexible metal, including for example stainless steel or nitinol hypotube. The stent 50, stop 56, ring 58, marker 60 are preferably made of any biocompatible material that is strong and rigid, including for example stainless steel, platinum, tungsten, etc. The components of the handle of the present invention are preferably made of a material that is strong and rigid, including for example inflexible polycarbonates, or even some metal components.

Of course, many different variations are included within the scope of the present invention. Some of these variations or alternative embodiments include any possible arrangement of sizes, materials, and designs within the bounds of the following claims.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A medical device delivery system for therapeutically treating a patient, comprising:

an inner shaft, having proximal and distal ends;

a tubular outer sheath, at least a portion of which surrounds a portion of the inner shaft member;

a medical device within the outer sheath in an initial configuration;

a handle affixed without relative movement to the inner shaft, and operatively coupled with tho outer sheath;

a first and second independently moveable actuator for adjusting the relative longitudinal positions the inner shaft and the outer sheath, each of the first and second actuators providing a different amount of mechanical advantage between an input to one of the first and second actuators by a physician and a resulting relative longitudinal position of the inner shaft and the outer sheath respectively.

2. The medical device delivery system of claim 1, wherein one of the first and second actuators provides a mechanical advantage of 1:1.

3. The medical device delivery system of claim 1, wherein the first actuator is adapted to rotate around a threaded base.

4. The medical device delivery system of claim 1, wherein the second actuator is adapted to slide along a longitudinal slot defined by the handle.

5. The medical device delivery system of claim 1, wherein on of the first and second actuators is formed as a lever.

6. The medical device delivery system of claim 1, wherein the first actuator provides a mechanical advantage greater than 1:1, to facilitate an operator to overcome initial resistance to changing the initial relative position of the inner shaft and the outer sheath.

7. The medical device delivery system of claim 1, wherein the handle and the first and second actuators can be operated by one hand.

8. The medical device delivery system of claim 1, further comprising a limit element limiting the extent of travel for the second actuator.

9. The medical device delivery system of claim 8, wherein the limit element resists relative rotation between the inner shaft member and the tubular outer sheath.

10. A handle for manipulating a medical device delivery system for therapeutically treating a patient, comprising:

a housing;

inner and outer shaft members;

the inner shaft member being firmly affixed to the housing;

the outer shaft member being movably coupled to the inner shaft member, such that the outer shaft member can be moved longitudinally with respect to the inner shaft member;

first and second independent means for selectively moving the outer shaft member with respect to the inner shaft member;

the first means being adapted for precise and sensitive adjustment of the position of the outer shaft member, and the second means being adapted for rapid and relatively large-scale movement of the outer shaft member.

11. A medical device delivery system for therapeutically treating a patient, comprising:

an inner shaft, having proximal and distal ends;

a tubular outer sheath, at least a portion of which surrounds a portion of the inner shaft member;

a medical device within the outer sheath in an initial configuration;

a handle firmly affixed to the inner shaft and operatively coupled with the outer sheath;

a first and second independently moveable actuator for adjusting the relative longitudinal positions of the inner shaft and the outer sheath, each of the first and second actuators providing a different amount of mechanical advantage between an input to one of the first and second actuators by a physician and a resulting relative longitudinal position of the inner shaft and the outer sheath respectively;

a limit element limiting the extent of travel for the second actuator, wherein the limit element resists relative rotation between the timer shaft member and the tubular outer sheath.

* * * * *